United States Patent
Fleute et al.

(10) Patent No.: US 7,227,981 B1
(45) Date of Patent: Jun. 5, 2007

(54) THREE-DIMENSIONAL STATISTIC RECONSTRUCTION OF SURFACES

(75) Inventors: Markus Fleute, Saint Martin d'Heres (FR); Stéphane Lavallee, Grenoble (FR); Laurent Desbat, Grenoble (FR)

(73) Assignee: Universite Joseph Fourier (FR)

( * ) Notice: Subject to any disclaimer, the term of this patent is extended or adjusted under 35 U.S.C. 154(b) by 475 days.

(21) Appl. No.: 10/088,772

(22) PCT Filed: Sep. 14, 2000

(86) PCT No.: PCT/FR00/02546

§ 371 (c)(1),
(2), (4) Date: Jul. 30, 2002

(87) PCT Pub. No.: WO01/22368

PCT Pub. Date: Mar. 29, 2001

(30) Foreign Application Priority Data

Sep. 17, 1999 (FR) .................................. 99 11848

(51) Int. Cl.
*G06K 9/00* (2006.01)
(52) U.S. Cl. ...................... 382/132; 382/128; 382/154
(58) Field of Classification Search ........ 382/128–134, 382/254, 154, 266, 102, 285
See application file for complete search history.

(56) References Cited

U.S. PATENT DOCUMENTS 4,630,203 A * 12/1986 Szirtes ....................... 382/132
5,905,809 A * 5/1999 Timmer ..................... 382/131
6,106,466 A * 8/2000 Sheehan et al. ............ 600/443

OTHER PUBLICATIONS

Lavallee et al., "Recovering the Position and Orientation of Free-Form Objects from Image Contours Using 3D Distance Maps," IEEE, 1996, pp. 378-390.*
Fleute et al., "Building a Complete Surface Model from Sparse Data Using Statistical Shape Models: Application to Computer Assisted Knee Surgery", MICCAI, 1998, pp. 879-887.*
Fleute, M.; Lavallee, S.: "Building a Completed Surface Model from Sparse Data Using Statistical Shape Models: Application to Computer Assisted Knee Surgery", Medical Image Computing and Computer-Assisted Intervention—Miccai '98 Proc., Oct. 1, 1998, XP00913649, Cambridge, MA, USA cite dans la demande, abrege, Figures 1-4, p. 880, alinea 2-p. 885, ligne 4.

(Continued)

*Primary Examiner*—Matthew C. Bella
*Assistant Examiner*—Shefali Patel
(74) *Attorney, Agent, or Firm*—Duane Morris LLP

(57) ABSTRACT

The invention concerns a method and a system for three-dimensional reconstruction of an image representing the surface contours of at least an object (1), from at least a two-dimensional view of said object obtained by X-ray, which consists in: determining the position of the photographing source (7) in a reference repository; selecting a predefined model constituting a mean form of the object, and repeating the process until the contours of the model are such that the variations between the overhead projection rays of the contours of the two-dimensional image from the source and the model surface are minimal; selecting an orientation and a position for the model in the reference repository; then selecting a deformation of the model to modify its contours in three dimensions.

10 Claims, 3 Drawing Sheets

OTHER PUBLICATIONS

Lavallee. S/ et al.: "Recovering the Position and Orientation of Free-Form Objects From Image Contours Uisng 3D Distance Maps" IEEE Transactions on Pattern Analysis and Machine Intelligence, US, IEEEE Inc. New York, vol. 17, No. 4, Apr. 1, 1995, pp. 378-390, XP000499568 ISSN: 0162-8828 p. 378, 379 figures 2-4, p. 385 and 387.

Gueziec, A., Kazanzides, P., et al.: "Anatomy-Based Registration of CT-scan and Intraoperative X-Ray Images for Guiding a Surgical Robot" IEEE Trans. Med. Imag., vol. 17, No. 5, Oct. 1, 1998, pp. 715-728, XP002140303, Figures 1,5, p. 718 and p. 720.

Lavallee. S. et al.: "Matching of Medical Images for Computed and Robot Assisted Surgery" Proceedings of the Annual International Conference of the Engineering in Medicine and Biology Society, US, New York, IEEE, vol. CONF. 13, 1991, pp. 39-40, XP000347734.

* cited by examiner

THREE-DIMENSIONAL STATISTIC RECONSTRUCTION OF SURFACES

This application is filed under 35 U.S.C. § 371 and claims priority rights under 35 U.S.C. §§ 119 and 365 from International application number PCT/FR00/02546, filed on Sep. 14, 2000, and from French application 99/11848, filed on Sep. 17, 1999, the entire disclosures of which are hereby incorporated by reference.

The present invention relates to the restoring of three-dimensional images and, more specifically, to the restoring of the surface contours of an image based on two-dimensional views, even incomplete.

An example of application of the present invention is the restoring of images representing bone elements from two-dimensional images taken, for example, with X-rays. Such images may be used, for example, to simulate a surgical intervention by enabling the practitioner to pre-visualize the respective positions of the bones at the level of a joint, for example, in case of a ligamentary plastic surgery or of the placing of a prosthesis.

Currently, to enable a practitioner to visualize a three-dimensional image based on two-dimensional images, an X-ray scanner performing tomographies must be used. Based on the tomographies, a three-dimensional image can be restored. The involved technology may be a so-called three-dimensional tomography technology in which a large number of views (on the order of 200) are taken by means of an X-ray scanner according to different positions, and the bone contours are then restored by image processing based on these scanner views. It may otherwise be a so-called two-dimensional tomography technology in which a large number of cross-sections are taken by means of an X-ray scanner at right angles to the bone. The shape and structure of the bone can then be restored.

The scanner technique provides good results but has a heavy and expensive implementation. Indeed, the use of a scanner enables obtaining a set of two-dimensional images providing information not only about the contour, but also about the inside of the bone. Now, in many applications, only the knowledge of the surface contour of the bone or of the object is necessary.

Another example of application of the present invention is the restoring of incomplete bones, for example, in archeology. A three-dimensional image restoring may enable almost perfectly finding the original bone shape, even if said bone is incompletely discovered. In such an application, problems similar to those discussed hereabove in relation with the simulation of surgical interventions are posed. In particular, it is often useful to know the shape of the bone without having to consider its internal structure.

Another disadvantage of known techniques is that they impose a high radiation dose for the patient, which is not desirable. If this disadvantage is less significant in the field of archeology, where cost is the main parameter, it is particularly disturbing in the simulation of surgical interventions.

The present invention more specifically applies to the restoring of images relating to identified objects, that is, the general shape of which is known in advance. For example, for a bone, which bone is involved must previously be decided.

The present invention aims at providing a novel method for restoring three-dimensional images, which overcomes the disadvantages of known techniques. The present invention aims, in particular, at providing a solution which does not require the expensive use of an X-ray scanner.

The present invention also aims at providing a solution which is compatible with a minimum exposure to X-rays or the like.

The present invention further aims at minimizing the number of two-dimensional views necessary to restore the three-dimensional image.

To achieve these objects, the present invention provides a method for restoring a three-dimensional image representing the surface contours of at least one object, based on at least one two-dimensional X-ray view of this object, characterized in that it consists of:

determining the position of the shooting source in a reference referential system;

selecting a predefined model forming an average shape of the object; and iteratively, until the contours of the model are such that the intervals between back-projection rays of the image contours in two dimensions from the source and the model surface are minimum:

selecting an orientation and a position of the model in the reference referential system, then selecting a deformation of the model to modify its contours in three dimensions.

According to an embodiment of the present invention, the model is obtained based on an object population for which the statistical correspondence common to all objects is searched to determine an average shape and the main deformations with respect to this average shape, to have at least one statistical model.

According to an embodiment of the present invention, the iterative selection steps consist of submitting the statistical model, successively, to a rigid transformation modifying its position and/or its orientation and to a non-rigid deformation modifying its surface contours.

According to an embodiment of the present invention, the image contours in two dimensions are automatically obtained by projecting the model in the image plane in two dimensions, and by deforming the projected contours to have them coincide with the points of strong grey level gradient of the two-dimensional image.

According to an embodiment of the present invention, the automatic determination of the image contours in two dimensions is performed iteratively, each iteration being interposed between two successive iterations of the selection steps.

According to an embodiment of the present invention, three-dimensional coordinates of points of the object are determined in the reference referential system, to have additional reference points for the iterative position, orientation, and deformation selection steps.

According to an embodiment of the present invention, several two-dimensional images, for which the respective positions of the shooting source are all determined in the reference referential system, are used, and the iterative selection steps are performed while taking account of the back-projection rays of the contours of all the two-dimensional images.

According to an embodiment of the present invention, the number of used images is a function of the desired accuracy.

According to an embodiment of the present invention, the model surface is formed of triangle elements, said intervals being measured with respect to points of given edges forming generators of the three-dimensional contour.

According to an embodiment of the present invention, the method is applied to the restoring of the surface contours of several objects linked together by rigid and/or resilient transformation relations.

According to an embodiment of the present invention, the method is applied to the restoring of bone images.

The present invention also relates to an image processing system, including means for implementing the three-dimensional image restoring method.

These and other objects, features and advantages of the present invention will be discussed in detail in the following non-limiting description of specific embodiments in connection with the accompanying drawings, in which.

Figure 3A:
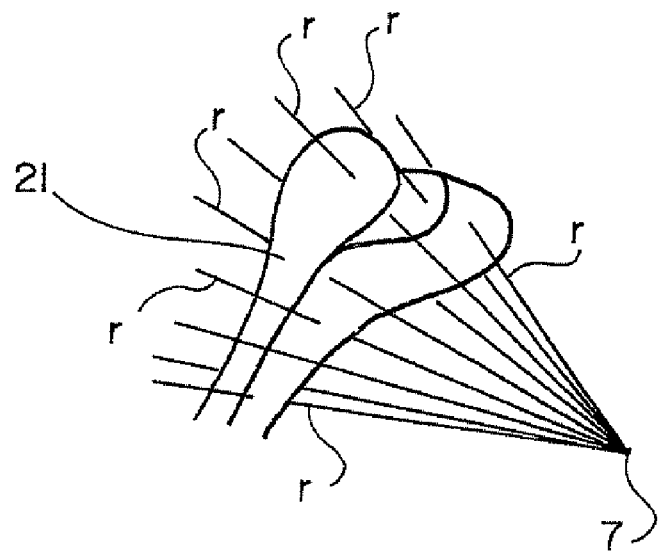
Figure 3B:
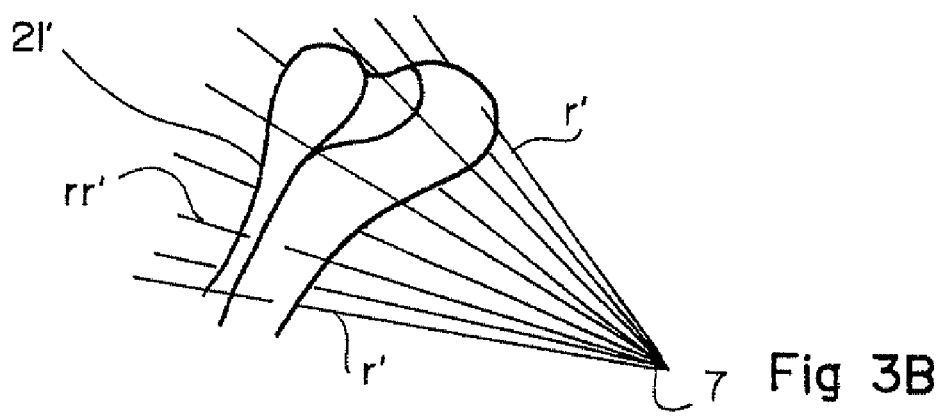
Figure 3C:
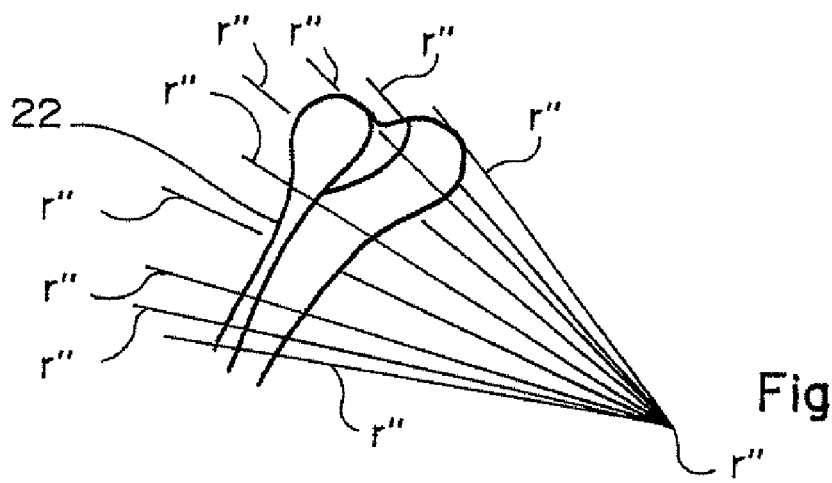
Figure 4:
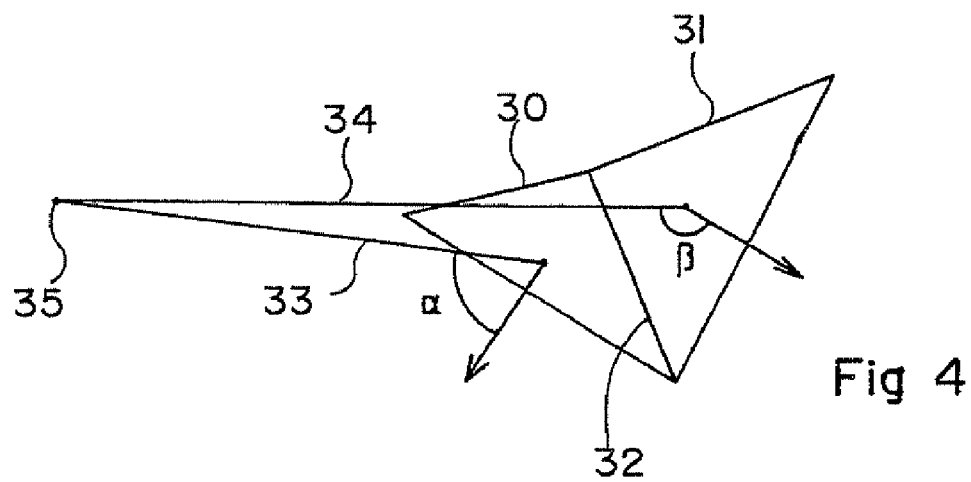
Figure 5:
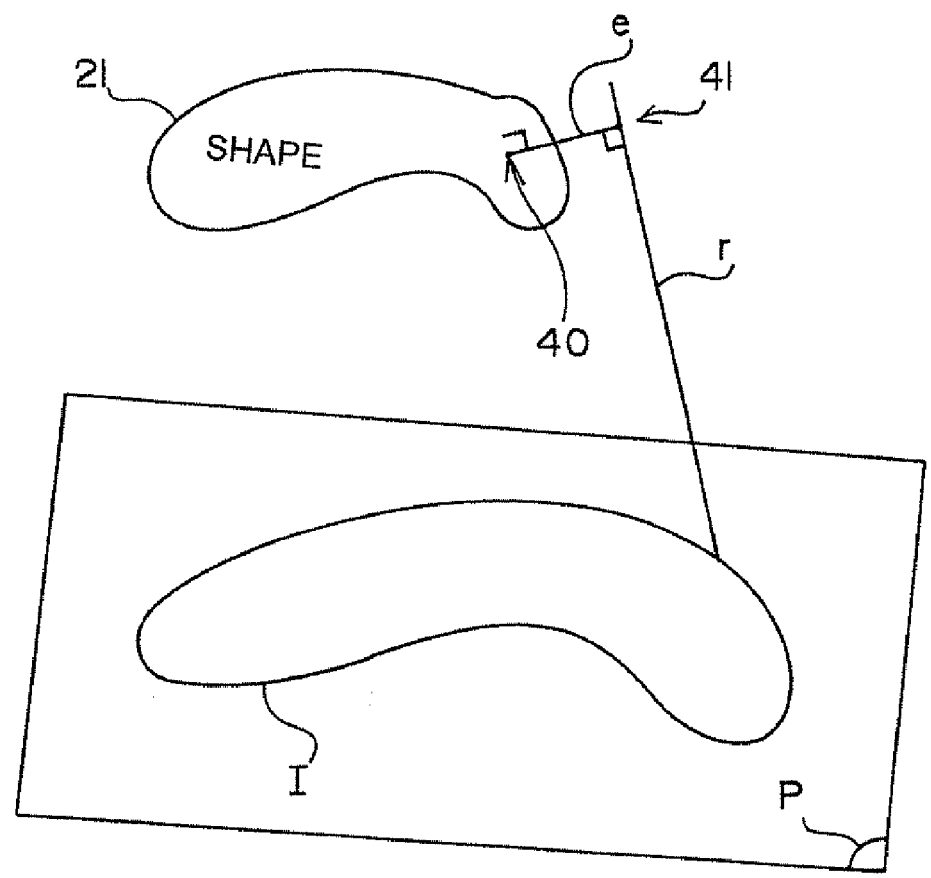

FIGS. 3A, 3B, and 3C illustrate three characteristic steps of the method according to an embodiment of the present invention;

FIG. 4 illustrates a mode of contour generator determination according to the present invention; and FIG. 5 illustrates a preferred mode of determination according to the present invention of the interval between a three-dimensional model and a two-dimensional view.

The same elements have been referred to with the same references in the different drawings. For clarity, only those elements of the supply system which are necessary to the understanding of the present invention have been shown in the drawings and will be described hereafter. In particular, the image processing means including the computer have not been shown and will not be described in detail, since their implementation is within the abilities of those skilled in the art based on the functional indications given hereafter.

A feature of the present invention is to search the position and the orientation of an object to be restored, at least one two-dimensional view of which is known, based on a database containing models of this object. When several two-dimensional views are used, these views are all referenced in a same referential system. Thus, the present invention relates to the restoring of an image representing an already identified object, of which models of different size and/or shape may be available.

A feature of a preferred embodiment of the present invention is to use at least one deformable statistical model, established based on the database, to restore the three-dimensional shape of the object. Thus, the present invention provides defining, before any restoring, a database containing three-dimensional models of the object to be restored or, preferably, one or several deformable statistical models based on this database.

Figure 1:
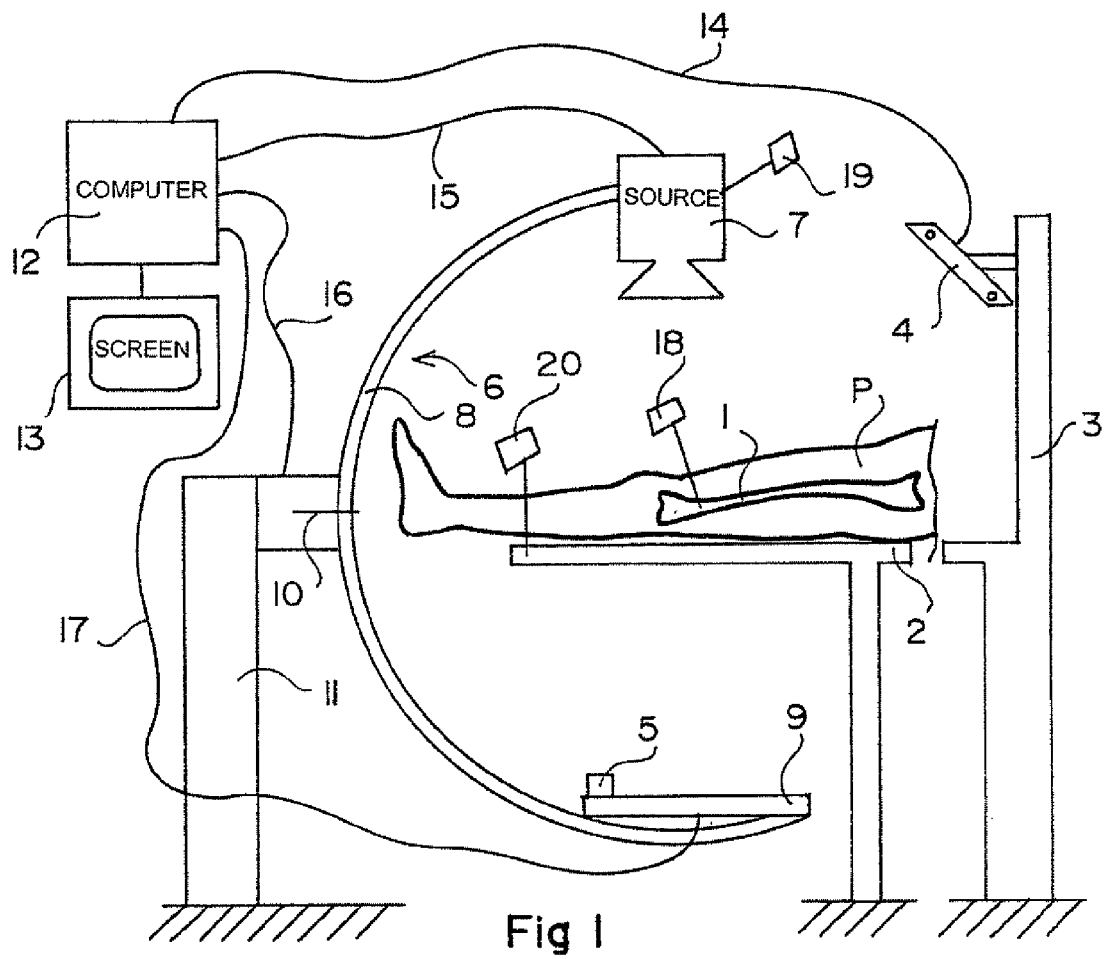
FIG. 1 shows an embodiment of a system of three-dimensional image restoring based on a two-dimensional shooting device according to the present invention.

FIG. 1 shows a simplified view of a three-dimensional image restoring system according to an embodiment of the present invention. The example of FIG. 1 relates to the restoring of image 1 of a bone based on two-dimensional radiographies. In FIG. 1, the body of a patient p, the leg of whom contains bone 1 which is desired to be visualized, has been shown. The leg of patient p (and thus bone 1) is, for example, laid on a table 2. A support 3 supports a three-dimensional localization device 4 which may be an optical, magnetic, mechanical, or ultrasound device, and which locates the position and orientation of multiple sensors-transmitters formed, for example, of infrared diodes, of reflectors, of magnetic, ultrasound transmitters, etc. Such a localizer is perfectly well known and will not be detailed any further. It should only be noted that, to guarantee a correct localization of the patient (of bone 1), he is generally also equipped with a sensor-transmitter 18 detectable by localizer 4. Indeed, according to the present invention, all views must be exploitable in a same (reference) referential system, which is associated with the object being restored.

Several sensors-transmitters may be attached on the radiology system, close to source 7 (sensor-transmitter 19) or close to an image detector 9 (sensor-transmitter 5), to locate the position of the radiology system with respect to the reference referential system of sensor-transmitter 18.

In some cases, sensors-transmitters 5 and 19 are difficult to locate due to their remoteness or to the presence of parasitic objects in the measurement field of localizer 4. In this case, a sensor-transmitter 20 may be installed on table 2 in the measurement field of localizer 4. The radiological system is then positioned in good measurement conditions and the positions of sensors-transmitters 5 and 19 are located with respect to sensor-transmitter 20 once and for all (this step is only renewed if the entire radiology system is moved).

The radiological system being equipped with angular coders on its axes, as will be detailed hereafter, the changes of relative position of the radiological system are measured by means of these coders and can thus be plotted in the referential system of sensor-transmitter 20. For each shooting, the geometric relation between sensors-transmitters 20 and 18 is measured and, by this means, the position of the radiological system is plotted in the reference referential system of sensor-transmitter 18. Thus, all radiographies are calibrated in the referential system of sensor-transmitter 18, which may be mobile.

Device 6 is, for example, formed of an X-ray source 7 supported by a first end of an arm 8 in a half-circle, the other end of which is intended to receive impression film 9 of the radiography, or an equivalent electronic sensor such as a brightness amplifier, or a flat amorphous silicon detector. The relation between arm 8 and table 2 is such that the latter is located between source 7 and sensor 9. Arm 8 is rotatably assembled around an axis 10, motorized or hand-moved, and supported by a support 11. The two-dimensional shooting assembly can thus rotate around bone 1 to perform the desired number of radiographies thereof. If necessary, optical localizer 4 may be associated with a device of angular coding of the position of axis 10.

The assembly is driven by a computer system, for example, a computer 12 associated, preferably, with a visualization screen 13. In FIG. 1, the computer buses for exchanging electric control and data signals between computer 12 and, respectively, localizer 4, source 7, the motor or the optional coder of axis 10, and sensor 9 have been symbolized by single-wire connections 14, 15, 16, and 17.

Figures 2A, 2B:
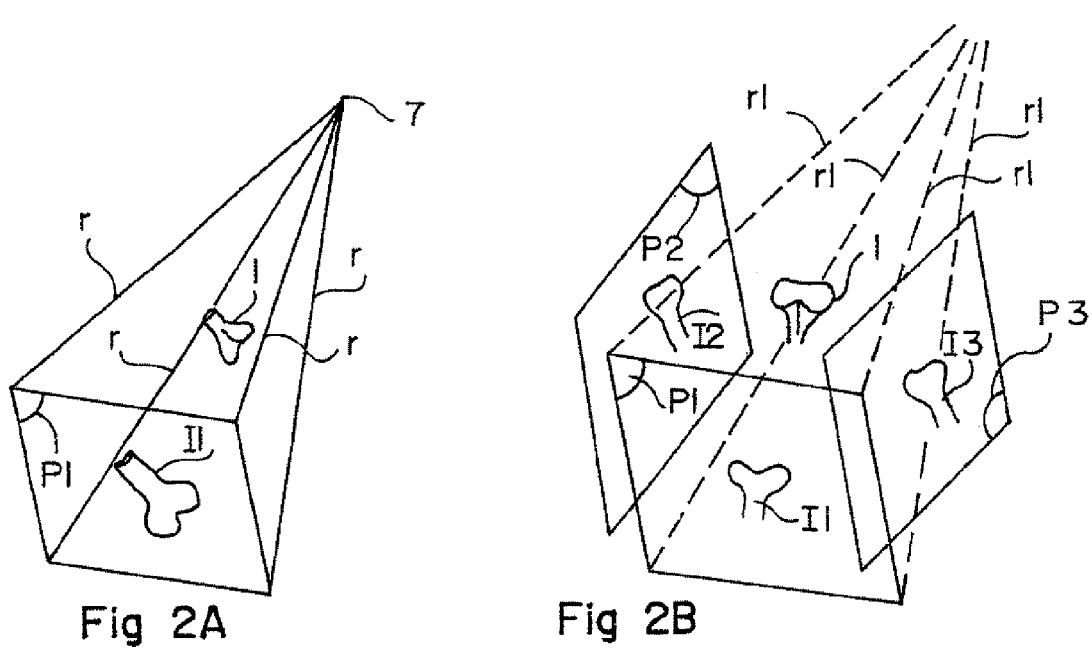
FIG. 2A illustrates the taking of a two-dimensional view to implement the three-dimensional image restoring method according to the present invention.
FIG. 2B illustrates the taking of three two-dimensional views to implement the restoring method according to the present invention.

FIGS. 2A and 2B illustrate two shooting modes according to two embodiments of the present invention. In FIGS. 2A and 2B, the two-dimensional views have been represented by the respective planes in which they are taken, that is, by the shape of the surface of sensor 9 (FIG. 1) in the shootings. This corresponds to the two-dimensional radiographic images recovered by the computer system.

FIG. 2A shows the case of a single shooting in a plane P1, providing an image I1 of bone 1. The position of source 7 has been symbolized by a point where back-projection rays r from the four corners of plane P1 converge.

FIG. 2B shows the case of a triple shooting in planes P1, P2, and P3, providing three images 11, 12, and 13 in two dimensions of bone 1. In FIG. 2B, the source position is not constant, it being different for each shooting. However, due to localizer 4, all source positions are known in the reference referential system. For clarity, only rays r1 from the four corners of plane P1 in the position of image I1 have been shown.

It should be noted that the shooting source may be submitted, between two two-dimensional images, to motions other than in a same plane as illustrated in FIGS. 1 and 2B. In other words, arm 8 of shooting system 6 may have more than two degrees of liberty, each of which may be provided with an angular coding device. According to a preferred embodiment, arm 8 is assembled on two horizontal and vertical rotation axes and one vertical translation axis.

It should also be noted that the two-dimensional images may be only partial. For example, in the application to radiographies, said radiographies may be interpreted by the operator to validate the contours of the two-dimensional views to be taken into account for the restoring. Such an interpretation is not disturbing due to the small number of two-dimensional views necessary according to the present invention (generally, less than ten). The validation of the contours in the computer system may be performed, for example, by means of a mouse, of a lightpen, of a tactile screen, or the like, conventionally for a contour recording on a grey level image.

According to another preferred embodiment, the determination of the contours on the radiographic images is automated by implementing a so-called two-dimensional adjustment method. Such a method consists of automatically determining the contour by analyzing the strongest grey level gradients. This method is described, for example, in Gelu Ionescu's thesis, publicly disclosed on Dec. 4, 1998, at the Joseph Fourier University, Grenoble (France), and entitled "Segmentation et recalage d'images échographiques par utilisation de connaissances physiologiques et morphologiques". According to the present invention, this two-dimensional adjustment method is implemented in combination with a projection, on the two-dimensional image, of the deformable statistical model of the object of which the surface contours are desired to be restored in three dimensions. An iterative analysis of a projected contour of the model on the two-dimensional image is performed until obtaining, after several runs (for example, from 3 to 10), an identity between the contour of the projected model which will be described hereafter, and the orientation and the deformation of which will have been adapted by the method of the present invention, and the contour determined by analysis of the strongest grey level gradients. This combination will be better understood hereafter in relation with FIG. 5.

To simplify the present description, it will be considered hereafter that the contours of the two-dimensional views are known. In practice, the steps of the method of the present invention will be performed in a loop, including the two-dimensional adjustment, until a satisfactory result is obtained.

According to the present invention, once the two-dimensional view(s) have been obtained, the shape and size of the three-dimensional object (here, the bone) remain to be determined by matching search in the database.

For this purpose, the present invention provides searching for the model for which the distances separating the contours of each two-dimensional view and the model surface are minimum.

In the preferred embodiment where a deformable statistical model (thus defining a model family) of the object to be restored is used, it is desired to come as close as possible, by iterative deformation of this model, to the shape having contours such that, as will be seen hereafter in relation with FIG. 5, the back-projection rays crossing on the points of the two-dimensional image contour from the source (or from their respective sources) are all tangential to the model surface, it being understood that the different two-dimensional contours are locatable in the reference referential system.

The implementation of the actual deformable statistical model is no object of the present invention and is perfectly conventional. It should only be reminded that the implementation of such a model generally uses a search for an average shape of a population of objects of same type (for example, femurs) forming the database, followed by a main component analysis to determine the main (essential) deformations to be applied to the average shape and thus obtain the statistical model.

A method for determining a statistical model from a sample family is described, for example, in article "Building a Complete Surface Model from Sparse Data Using Statistical Shape Models: Application to Computer Assisted Knee Surgery" by Markus Fleute and Stéphane Lavallée, published in MEDICAL IMAGE COMPUTING AND COMPUTER-ASSISTED INTERVENTION—MICCAI'98, Springer-Verlag LNCS Series, pages 880–887, October 1998, the content of which is incorporated herein by reference. It should be noted that the accuracy of the reconstruction of the surface contours performed by the present invention depends on the samples used to build the database of the statistical model. For example, if a statistical model of a femur is created based on a sample population having normal shapes (with no pathology), normal shapes can be accurately restored, but the accuracy will be limited if the radiographed femur has a pathological shape. However, if the statistical model is created based on a large population of samples containing both normal shapes and pathological shapes, normal and pathological objects may be accurately restored.

According to the present invention, once two-dimensional images are available, it may be searched to which model contained in the database these images are closest (for example, if several types of bones or if several statistical models of a same bone are available), after which transformations are applied to this model to come as close as possible to a three-dimensional image, such that the back-projection rays of the images to their respective sources are tangential to the surfaces of the three-dimensional image, placed on the path of these rays and to which they are respectively closest.

Preferably, the initial model at rest, that is, corresponding to the average shape, is submitted to a so-called rigid transformation, that is, only concerning its orientation and its shifting in space. Then, when the position for which the back-projection rays all are at a minimum distance from the contours of the initial model has been obtained, the model is submitted to a non-rigid deformation, that is, without modifying its orientation, its shape is modified based on the data contained in the statistical base by modifying the coefficients of the main modes of the model, to obtain the shape having the closest contours to the back-projection rays. If necessary, the model is very approximately prepositioned by the operator with respect to the two-dimensional views displayed on screen. It should be noted that the used image processing (computer) means are conventional in their structure and thus do not require being detailed.

FIGS. 3A to 3C illustrate these two steps of the method of the present invention. FIG. 3A shows a three-dimensional view of a model 21 before any deformation. It is, for example, a statistical model of the present invention positioned by the practitioner in an approximate orientation. FIG. 3B shows model 21' of FIG. 3A at the end of the orientation step with no shape modification. FIG. 3C shows image 22 in three dimensions resulting from the implementation of the present invention, that is, corresponding to model 21', deformed so that the back-projection rays are (ideally) tangent to all its contours.

For simplification, a single group of back-projection rays r from a source 7 have been shown in FIGS. 3A to 3C and the projection screen of the corresponding image has not been shown. As appears from FIGS. 3A to 3C, a large number of rays r of FIG. 3A are not tangent to the contours of model 21. The number of used back-projection rays depends on the desired accuracy and on the characteristics of the statistical model, essentially, on the number of surface points chosen to be used as a reference in the definition of this statistical model.

From FIG. 3A to FIG. 3B, the transformation is "rigid", that is, the model is not deformed. In this transformation, model 21 undergoes translations and rotations to obtain measurements of minimum intervals between each back-projection ray starting from the image contour points and the surface of the object in its current position. Mathematical methods for searching for the minimum of the sum of the squares of these intervals with respect to the six parameters (three degrees of liberty in rotation and three degrees of liberty in translation) defining the searched rigid transformation are used for this purpose. A configuration such as illustrated in FIG. 3B, in which model 21' has a proper position and orientation but a still imperfect shape is obtained. This is why some rays r' are not tangent but cross the model.

Preferably, the position resulting from the rigid transformation (rotation, translation) is obtained by a so-called iterative closest point (ICP) method (algorithm). An example of such a method is described in article "A Method for Registration of 3-D Shapes", by Paul J. Best and Neil D. McKay, published in IEEE TRANSACTIONS ON PATTERN ANALYSIS AND MACHINE INTELLIGENCE, vol. 14, N°2, February 1992, the content of which is incorporated herein by reference.

From FIG. 3B to FIG. 3C, the transformation is "non-rigid" (resilient) and consists of deforming model 21' without changing its orientation until obtaining three-dimensional image 22 for which all back-projection rays r" are at a minimum distance from the contours (ideally tangent). This non-rigid transformation is performed, for example and according to a first embodiment, by calculating the deformation parameters from an algorithm known as the "down hill simplex". This algorithm has been described, for example, in 1965 by J. A. Nelder and R. Mead in COMPUTER JOURNAL, vol. 7, pages 308–313, the content of which is incorporated herein by reference.

According to a preferred embodiment of the present invention, the algorithm used to determine the non-rigid transformation of the statistical model is based on the Levenberg-Marquardt method. The principle of this method is to determine the minimum of a multidimensional non-linear function by using the partial derivatives of the function with respect to the deformation parameters of the model. This method has been described, for example, in 1963, by D. W. Marquardt in JOURNAL OF THE SOCIETY FOR INDUSTRIAL AND APPLIED MATHEMATICS, vol. 11, pages 431–441, the content of which is incorporated herein by reference. The function of which the minimum is searched here is the sum of the squares of the distances between a set of back-projection rays based on the contour points and the model surface. The parameters of this search for the minimum are the coefficients which are applied to each deformation mode of the statistical model, as discussed in above-mentioned article "Building a Complete Surface Model from Sparse Data Using Statistical Shape Models: Application to Computer Assisted nee Surgery" by Markus Fleute and Stéphane Lavallée.

This method is applied and repeated at each approximated position until it is no longer possible to minimize the intervals. A rigid adjustment, a resilient adjustment, a rigid adjustment, a resilient adjustment, etc. are thus consecutively performed. Once the three-dimensional shape has been restored, its size is of course also known since all two-dimensional views have known sizes, and so is the position, in the reference referential system, of the model with respect to the sources. The number of necessary runs essentially depends on the number of characteristic parameters used to model the deformation.

It should be noted that the order in which the two above steps are performed is important. Indeed, if a non-rigid deformation is first performed, a model will be made to correspond to a wrong orientation, which will be very difficult to recover due to the shape deformation undergone. However, the interval minimization may be performed globally by taking into account the rigid parameters and the deformation parameters at the same time for each iteration of the mathematical minimization process.

It should be noted that, for each iterative step of the method in which the intervals between the model contours and the back-projection rays are calculated, new points entering in the measurement are determined on the model side and/or on the side of the projection rays. This is a significant distinction with respect to known three-dimensional image restoring methods in which the measurement points are the same for all iterations.

Another feature of the present invention is that the evaluations of the minimum intervals are not necessarily made exhaustively for all the surface elements of the model. Indeed, this would sometimes lead to too expensive calculations, even if the number of surface elements can be minimized by using triangular elements. According to the present invention, the interval evaluations are made with respect to characteristic lines forming contour generators of the model. This minimizes the number of measurement points. For example, a bone of femur type, defined by approximately 5000 triangular surface edges, is defined by approximately 300 contour generators.

Preferably, the analysis performed by the method of the present invention only concerns contour generators of the three-dimensional image. Thus, the surface of the statistical model is, preferably, formed of triangular elements, some edges of which define generators of the contour. A contour generator is defined by the edges of the triangles which, projected on a plane, define the contour (internal or external). The use of contour generators enables considerably reducing (for example, by at least a factor 10) the number of points to be searched in the model to check the correspondence with the restored image.

FIG. 4 illustrates the definition of a contour generator of a three-dimensional image (model), the surface of which is formed of triangular surface elements such as described, for example, in article "Anatomy-based registration of ct-scan and intraoperative x-ray images for guiding a surgical robot" by A. Gueziec, published in IEEE TRANSACTIONS ON MEDICAL IMAGING, 17(5), pages 715–728, October 1998, the content of which is incorporated herein by reference.

FIG. 4 shows in a simplified manner two triangles 30 and 31 defining a portion of the surface of a three-dimensional model, the common edge of which forms a generator 32 of the contour. The calculation to be performed to determine whether an edge is or not a generator of the contour consists of calculating the respective angles α and β between the lines perpendicular to the surfaces of triangles 30 and 31 and rays 33 and 34 linking the center of these surfaces to projection center 35 corresponding to the position of the X-ray source. If one of the angles is smaller than 90° while the other one is greater than 90°, their common edge 32 then is a generator of the contour.

FIG. 5 illustrates the type of measurement performed to determine interval e between a back-projection ray r and a point of a contour generator. This drawing schematically shows an image I of the object in plane P and a shape 21 of the statistical model placed on the path of the back-projection rays of image I to the source (not shown).

For each back-projection ray r, the respective points 41 and 40 of the back-projection ray and of a contour generator chosen from among all the generators, for which interval e between these points is minimum, are searched.

An advantage of the present invention is that it enables much faster restoring of a three-dimensional image than known techniques.

Another advantage of the present invention is that it enables proper alignment of the model even in areas where data of projection by the two-dimensional images are not available (for example, some internal curvatures).

It should be noted that the surface contour may, if necessary, be refined by means of a mechanical, optical, or magnetic feeler, providing space coordinates in the same referential system as the two-dimensional images. Additional points which can be used in the search for the three-dimensional image are then obtained. The feeler may be used, for example, to decrease the number of necessary two-dimensional views by giving a three-dimensional information.

It should also be noted that the method of the present invention may apply to several three-dimensional surface contours forming one or several objects. For example, the external surface and the internal cortical surface of a bone can thus simultaneously be restored. The shape of several bones taking part in a joint and simultaneously visible on the radiological images (for example, the tibia and the femur, if the knee is considered), or the shape of several bone fragments of a same bone, may also be restored. The searched model must, in this last case, contain the rigid transformations between each three-dimensional surface contour. In other cases of application to several objects, the different statistical models and the rigid or resilient transformations between them must of course be known.

Of course the present invention is likely to have various alterations and modifications which will occur to those skilled in the art. In particular, the number of two-dimensional views to be used for the restoring depends on the desired accuracy and on the model complexity. In some cases, a single two-dimensional view may be enough. Further, although the present invention has been described in relation with a mobile X-ray source, said source may be replaced with several fixed sources, provided that the constraint of obtaining two-dimensional images in a same referential system is respected. Further, the implementation of the present invention of course uses digital image processing techniques, the practical implementation of which is within the abilities of those skilled in the art based on the functional indications given hereabove and in the publications mentioned as references.

The invention claimed is:

1. A method for restoring a three-dimensional image representing the surface contours of at least one object, based on at least one two-dimensional X-ray projection of this object, the method comprising the steps of:
   determining the position of the shooting source in a reference referential system;
   selecting at least one statistical model defining an average shape of the object and its main deformations with respect to this average shape, the statistical model being calculated from an object population of a same type for which the statistical correspondence common to all objects is searched; and
   selecting an orientation and a position of the model in the reference referential system by submitting the statistical model, successively, to a rigid transformation modifying its position and/or its orientation, then
   selecting a deformation of the model to modify its contours in three dimensions, by submitting the statistical model to a non-rigid deformation modifying its surface contours,
   wherein the orientation and deformation selecting steps are performed iteratively, until the contours of the model are such that the intervals between back-projection rays of the image contours in two dimensions from the source and the model surface are minimum, in order to obtain a correspondence between the model and the image.

2. The method of claim 1, wherein the image contours in two dimensions are automatically obtained by projecting the model in the image plane in two dimensions, and by deforming the projected contours to have them coincide with the points of strong gray level gradient of the two-dimensional image.

3. The method of claim 2, wherein the automatic determination of the image contours in two dimensions is performed iteratively, each iteration being interposed between two successive iterations of the selection steps.

4. The method of claim 1, further comprising the step of determining three-dimensional coordinates of points of the object in the reference referential system, to have additional reference points for the iterative position, orientation, and deformation selection steps.

5. The method of claim 1, further comprising the steps of using several two-dimensional images for which the respective positions of the shooting source are all determined in the reference referential system, and performing the iterative selection steps while taking account of the back-projection rays of the contours of all the two-dimensional images.

6. The method of claim 5, wherein the number of used images is a function of the desired accuracy.

7. The method of claim 1, wherein the model surface is formed of triangle elements, said intervals being measured with respect to points of given edges forming generators of the three-dimensional contour.

8. The method of claim 1, wherein the method is applied to the restoring of the surface contours of several objects linked together by rigid and/or resilient transformation relations.

9. The method of claim 1, wherein the method is applied to the restoring of bone images.

10. An image processing system comprising means for implementing the method of claim 1.

* * * * *